United States Patent [19]

Schaefer

[11] Patent Number: 5,009,597
[45] Date of Patent: Apr. 23, 1991

[54] COMPOSITE DENTAL PROSTHESIS ELEMENT FORMED OF FILLED ACRYLATE/METHACRYLATE POLYMERS

[75] Inventor: Roland Schaefer, Friedrichsdorf, Fed. Rep. of Germany

[73] Assignee: Kulzer & Co. GmbH, Wehrheim, Fed. Rep. of Germany

[21] Appl. No.: 358,456

[22] Filed: May 25, 1989

Related U.S. Application Data

[63] Continuation of Ser. No. 162,098, Feb. 29, 1988, abandoned.

[30] Foreign Application Priority Data

Mar. 17, 1987 [DE] Fed. Rep. of Germany ....... 3708618

[51] Int. Cl.$^5$ .................... A61C 5/09; A61C 8/00; A61C 13/00
[52] U.S. Cl. .................... 433/212.1; 106/35; 433/167; 433/201.1; 433/222.1; 433/223; 433/228.1; 523/115
[58] Field of Search .............. 523/113, 115; 106/35; 433/171, 180, 199.1, 201.1, 202.1, 212.1, 222.1, 223, 228.1, 167

[56] References Cited

U.S. PATENT DOCUMENTS

| 4,029,632 | 6/1977 | Gross et al. ...................... 524/442 |
| 4,267,097 | 5/1981 | Michl et al. ...................... 524/786 |
| 4,281,991 | 8/1981 | Michl et al. ...................... 523/115 |
| 4,360,344 | 11/1982 | Colpitts ...................... 433/199.1 |
| 4,375,967 | 3/1983 | Schaefer ...................... 433/199.1 |
| 4,433,959 | 2/1984 | Faunce ...................... 433/201.1 |
| 4,521,193 | 6/1985 | Ciaolone ...................... 433/199.1 |
| 4,544,359 | 10/1985 | Waknine ...................... 522/14 |

FOREIGN PATENT DOCUMENTS

| 0166009 | 6/1984 | European Pat. Off. . |
| 2405578 | 2/1974 | Fed. Rep. of Germany . |
| 2403211 | 7/1975 | Fed. Rep. of Germany . |
| 2914537 | 4/1979 | Fed. Rep. of Germany . |
| 3413398 | 4/1984 | Fed. Rep. of Germany . |
| 1408265 | 10/1975 | United Kingdom . |
| 1488403 | 10/1977 | United Kingdom . |
| 2018666 | 4/1979 | United Kingdom . |
| 1576080 | 10/1980 | United Kingdom . |
| 2153681 | 8/1985 | United Kingdom . |
| 81/02254 | 8/1981 | World Int. Prop. O. . |

OTHER PUBLICATIONS

Acta Parodonrologica, vol. 11/Nr. 3:77–104/1982.
Marxkors/Meiners, Taschenbuch der zahnarztlichen Werk-Stoffkunds (Pocketbook (Handbook) of Dental Material), 2. Auflage (1982), Seiten 94, 95 (Copy enclosed).

Primary Examiner—Paul Lieberman
Assistant Examiner—Linda D. Skaling
Attorney, Agent, or Firm—Frishauf, Holtz, Goodman & Woodward

[57] ABSTRACT

Composite dental prosthesis elements formed of filled acrylate- and/or methacrylate-based polymers and comprising a core having high flexural strength and a high bending modulus and an abrasion-resistant jacket with a highly lustrous surface are suitable for temporary and semipermanent as well as permanent installation with crowns and bridges, for inlays and the like.

25 Claims, 1 Drawing Sheet

COMPOSITE DENTAL PROSTHESIS ELEMENT FORMED OF FILLED ACRYLATE/METHACRYLATE POLYMERS

This application is a Continuation of application Ser. No. 07/162,089, filed Feb. 29, 1988, now abandoned.

The present invention relates to a plastic dental prosthesis element having a jacket of plastic, containing a microdispersed silicon dioxide, comprising from 10-90% by weight, having a particle size of 0.01-0.4 micrometers, made from an acrylate- and/or methacrylate-based polymer.

Background: From German Patent Disclosure Document DE-OS 24 05 578, dental prosthesis elements—crowns, bridges, false teeth—are known the outer layer of which comprises a plastic containing amorphous silicic acid—preferably from 30-80% by weight—having a maximum particle size of 0.07 micrometers. This layer has high abrasion resistance and can be polished to a high luster. It is prepared from polymerizable mixtures of the amorphous silicic acid, in particular with esters of methacrylic acid, for example bis[4-(2-hydroxy-3-methacryloyloxypropoxy)]dimethylmethane, known as bis-GMA (see U.S. Pat. No. 3,066,112) and triethylene glycol dimethacrylate. Plastic-based dental materials containing amorphous silicic acid of this type, or some other inorganic filler of equivalent particle size, are also known as composites having microfine fillers, or microfillers.

From British Patent 1,488,403, dental prosthesis elements are also known the outer layer of which comprises a plastic containing a microfine inorganic filler, particularly silicon dioxide and/or aluminum oxide. The material for preparing the layer contains, as the polymerizable monomer and/or polymer, polystyrene, polyamide, epoxy compounds, polyurethane, monomeric and polymeric acrylates and methacrylates, or mixtures thereof, and from 10-90% by weight of the microfiller having a particle size of 0.01-0.4 micrometers.

Plastic bridges for semipermanent reconstruction, sheathed with conventional or microfine-filled crown and bridge plastic, are described in Acta parodontologica, Vol. 11, No. 3, 77-87, 1982. These bridges are reinforced with an injected polyester core and as a result have very good resistance to breaking. Nevertheless, in the view of the authors the development of new materials that are substantially more wear-resistant and more dimensionally stable and furthermore are capable of being worked up in a slenderer embodiment, is necessary.

Dental materials containing both conventional and microfine inorganic fillers—the term hybrid composites has become established for such dental materials—are described in International Patent Application WO-81/02254. They contain filler mixtures of hydrophobic silicon dioxide having a diameter of 0.01-0.04 micrometers and glass, for example radio-opaque barium- or strontium-containing glass, having a diameter of 2-30 micrometers. Bis-GMA or ethoxylated bisphenol A dimethacrylate and triethylene glycol dimethacrylate serve as polymerizable monomers. The material is used as a tooth filling materal and for veneering cast gold crowns, for example.

A method for the simple and fast production of plastic crown or plastic-coated metal crowns is described in German Patent Disclosure Document DE-OS 29 14 537. To this end, a photopolymerizable material is used, which contains acrylates and/or methacrylates and optionally an inorganic filler, preferably quartz, and fine silicic acid anhydride as a thickener for the monomers and as a precipitation inhibitor for the filler. The crowns are prepared by means of single to triple application of the photopolymerizable material upon the plaster mold or metal frame and brief exposure to light, in order to cure it. Both homogeneous and heterogeneous crown structures are described. The latter comprise plastic without inorganic filler and a thin coating of plastic with inorganic filler.

A photopolymerizable crown and bridge material that as filler preferably contains a mixture of very fine silicon dioxide (microdispersed silicon dioxide) and glass is known from European Patent Application 166 009. As monomers, reaction products of polyisocyanates with bisphenol-diglycidyl acrylates and methacrylates and additionally other acrylates and methacrylates of multivalent alcohols, either containing urethane groups or not, are used.

False tooth elements comprising a plastic core, a thin-walled metal frame surrounding it and a jacket, preferably comprising the same plastic (acrylic resin) as the core, are known from German Patent Disclosure Document DE-OS 34 13 398.

The Invention: It is the object of the invention to discover a dental prosthesis element having a jacket of a plastic containing microdispersed silicon dioxide as an inorganic filler, made from an acrylate- and/or methacrylate-based polymer, the core of which should have greater mechanical strength than the jacket and likewise should comprise plastic filled with inorganic filler.

Briefly, the dental prosthesis element with which this object is attained is characterized in that the jacket surrounds a core of a plastic, made from an acrylate- and/or methacrylate-based polymer, containing, as inorganic filler, from 30-90% by weight of a mixture of from 60-100% by weight of an inorganic filler material having a particle size of 0.7-5 micrometers and from 0-40% by weight of microdispersed silicon dioxide having a particle size of from 0.01-0.4 micrometers.

Preferably, the core contains from 60-85% by weight of the inorganic filler, and the filler comprises a mixture of from 80-90% by weight of inorganic filler material and from 10-20% by weight of microdispersed silicon dioxide.

The jacket preferably contains from 30-70% by weight of microdispersed silicon dioxide.

Microdispersed silicon dioxide having a particle size of from 0.01-0.04 micrometers has proved to be particularly effective.

Any inorganic filler that is used in plastic dental materials is suitable as the inorganic filler material. Silicon dioxide, lithium aluminum silicate glass and/or strontium aluminum silicate glass has proved to be particularly effective.

It has been found advantageous for the inorganic filler material and the microdispersed silicon dioxide - both that contained in the jacket and optionally that contained in the core —to be silanized, for example with 3-methacryloyloxypropyltrimethoxysilane.

The plastic of the core and jacket preferably comprises polymeric esters of acrylic acid and/methacrylic acid with bivalent and/or multivalent alcohols. Polymers of bis-GMA, ethoxylated bisphenol A diacrylate, ethoxylated bisphenol A dimethacrylate, triethylene glycol dimethacrylate, dodecanediol dimethacrylate, diurethane dimethacrylate prepared from 2-hydroxyethylmethacrylate and 2,2,4-trimethylhexamethylene diisocyanate, bis(acryloyloxymethyl)tricyclo[5.2.1.0$^{2,6}$]decane and/or bis(methacryloyloxymethyl)tricyclo[5.2.1.0$^{2,6}$]decane are particularly suitable. (For use of the last two compounds given in dental compositions, see German Patent 28 16 823.)

For the core, polymers of esters of acrylic acid and/or methacrylic acid with bivalent and/or multivalent alcohols, comprising 20–85% by weight of bis-GMA or ethoxylated bisphenol A dimethacrylate, have proved to be particularly effective.

The plastic of the jacket preferably contains a polymer of bis(methacryloyloxymethyl)tricyclo[5.2.1.0$^{2,6}$]-decane and/or diurethane dimethacrylate of 2-hydroxyethylmethacrylate and 2,2,4-trimethylhexamethylene diisocyanate, optionally together with a polymer of dodecanedioldimethacrylate.

Additionally, polymers of esters of acrylic acid and/or methacrylic acid with bivalent and/or multivalent alcohols, comprising 30–80% by weight of diurethane dimethacrylate from 2-hydroxyethylmethacrylate and 2,2,4-trimethylhexamethylene diisocyanate, and esters, as well as of esters of acrylic acid and/or methacrylic acid with bivalent and/or multivalent alcohols, comprising 20–70% by weight of diurethane dimethacrylate from 2-hydroxyethylmethacrylate and 2,2,4-trimethylhexamethylene diisocyanate and 20–40% by weight of bis(methacrylotyloxymethyl)tricyclo[5.2.1.0$^{2,6}$]decane, have proved to be particularly effective.

The dental prosthesis element according to the invention can be polished to a high luster and has high abrasion resistance, flexural strength (core: approximately 120 to 200 MPa), breakage resistance and dimensional stability, so that it can be used both for temporary and semipermanent installation and for permanent installation of crowns and bridges. It is equally well suited, for example, as an inlay.

The very good mechanical properties allow, among others, thin-walled shapes—an advantage when there is little space available for installing crowns—and slender embodiments, such as for the interdental connection zones between the crown and the bridge, in the case of bridges with full-tooth bridge members.

A three-member bridge with a full-tooth bridge member of this type is shown in FIGS. 1 and 2, as an example of a dental prosthesis element according to the invention.

DETAILED DESCRIPTION

Figure 1:
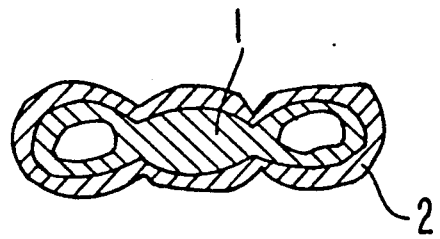
FIG. 1 shows the bridge comprising the core 1 and the jacket 2 in plan view.
Figure 2:
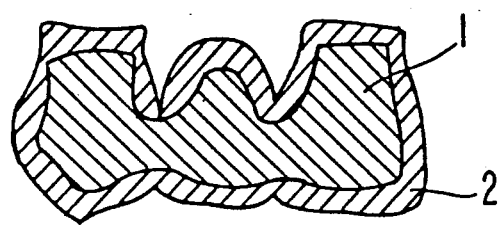
FIG. 2 shows the bridge in cross section.

The dental prosthesis element is prepared from mixtures henceforth called core material and jacket material, containing monomeric esters of acrylic acid and/or methacrylic acid with bivalent and/or multivalent alcohols, particularly bis-GMA, ethoxylated bisphenol A diacrylate, ethoxylated bisphenol A dimethacrylate, triethylene glycol dimethacrylate, dodecanediol dimethacrylate, diurethane dimethacrylate from 2-hydroxyethylmethacrylate and 2,2,4-trimethylhexamethylene diisocyanate, bis(acryloyloxymethyl)tricyclo[5.2.1.0$^{2,6}$]decane and/or bis(methacryloyloxymethyl)tricyclo[5.2.1.0$^{2,6}$]decane, which contain inorganic fillers and catalysts that bring about the photopolymerization.

As photopolymerization catalysts, the mixtures of ketones and amines, in particular of camphor quinone and amines, or mixtures of camphor quinone, benzil acetals and amines, for example p-dimethylaminoethyl benzoate, known from British Patent 1,408,265, have proved particularly effective. Upon exposure to light having a wavelength of 320–500 nanometers, they trigger the polymerization of the monomers.

Preferably both the core material and the jacket material each contain from 0.1–0.5% by weight of the camphor quinone, of the amine and optionally of the benzil acetal.

For further explanation, preferred compositions of the core material and jacket material and the preparation of a dental prosthesis element according to the invention are described in the following examples, using the Dentacolor XS lamp made by Kulzer for the photopolymerization of the core and the jacket material. The jacket material contains some of the microdispersed silicon dioxide in the form of a splinter polymerizate, filled therewith, of 55% by weight of microdispersed silicon dioxide, particle size 0.04 micrometers, silanized with 3-methacryloyloxypropyltrimethoxysilane, and 45% by weight of dodecanedioldimethacrylate.

EXAMPLE 1

Core material
4.5% by weight of bis-GMA
10.5% by weight of triethylene glycol dimethacrylate
72.6% by weight of lithium aluminum silicate glass, particle size 5 micrometers
12.0% by weight of microdispersed silicone dioxide, particle size 0.04 micrometers
0.1% by weight of camphor quinone
0.1% by weight of benzil dimethylacetal
0.2% by weight of p-dimethylaminoethyl benzoate

EXAMPLE 2

Core material
12.4% by weight of ethoxylated bisphenol A diacrylate
2.8% by weight of trimethylolpropane triacrylate
71.2% by weight of lithium aluminum silicate glass, particle size 5 micrometers
13.2% by weight of microdispersed silicone dioxide, particle size 0.04 micrometers, silanized with 3-methacryloyloxypropyltrimethoxysilane
0.1% by weight of camphor quinone
0.1% by weight of benzil dimethylacetal
0.2% by weight of p-dimethylaminoethyl benzoate

EXAMPLE 3

Core material
12.1% by weight of ethoxylated bisphenol A dimethacryate
3.0% by weight of hexamethylenedioldimethacrylate
79.8% by weight of lithium aluminum silicate glass, particle size 5 micrometers
4.7% by weight of microdispersed silicone dioxide, mean particle size 0.04 micrometers, silanized with 3-methacryloyloxypropyltrimethoxysilane
0.1% by weight of camphor quinone
0.1% by weight of benzil dimethylacetal
0.2% by weight of p-dimethylaminoethyl benzoate

EXAMPLE 4

Jacket material 11.3% by weight of diurethanedimethacrylate from 2 moles of 2-hydroxyethylmethacrylate and 1 mole of 2,2,4-trimethylhexamethylene diisocyanate (Plex 6661 made by Röhm, Darmstadt, Federal Republic of Germany)

7.6% of bis-GMA 3.4% by weight of triethylene glycol dimethacrylate 27.0% by weight of microdispersed silicone dioxide, particle size 0.04 micrometers, silanized with 3-methacryloyloxypropyltrimethoxysilane 50.0% by weight of splinter polymerizate, particle size 40 micrometers 0.1% by weight of camphor quinone 0.1% by weight of benzil dimethylacetal 0.2% by weight of p-dimethylaminoethyl benzoate 0.3% by weight of pigments

EXAMPLE 5

Jacket material 19.3% by weight of bis(acryloyloxymethyl)tricyclo[5.2.1.0$^{2,6}$]decane 28.1% by weight of microdispersed silicone dioxide, particle size 0.04 micrometers, silanized with 3-methacryloyloxypropyltrimethoxysilane 52.0% by weight of splinter polymerizate, particle size 40 micrometers 0.1% by weight of camphor quinone 0.1% by weight of benzil dimethylacetal 0.2% by weight of p-dimethylaminoethyl benzoate 0.2% by weight of pigments

EXAMPLE 6

Jacket material 19.3% by weight of bis(methacryloyloxymethyl)-tricyclo[5.2.1.0$^{2,6}$]decane 28.1% by weight of microdispersed silicone dioxide, particle size 0.04 micrometers, silanized with 3-methacryloyloxypropyltrimethoxysilane 52.0% by weight of splinter polymerizate, particle size 40 micrometers 0.1% by weight of camphor quinone 0.1% by weight of benzil dimethylacetal 0.2% by weight of p-dimethylaminoethyl benzoate 0.2% by weight of pigments

EXAMPLE 7

Core/Jacket Crowns

1. Insulation of the model stumps, for example with alginate or silicone insulation.
2. Modelling of the core material over one or more model stumps, layer thickness 0.3–0.6 mm.
3. Curing or intermediate polymerization of the core material to make a load-bearing layer by exposure to the lamp for 90 seconds.
4. Full buildup of the crown with the jacket material in a layer thickness of from 0.8–1.2 mm over the intermediately polymerized core material.
5. Final polymerization by means of exposure to the lamp for 180 seconds.
6. Finishing and polishing to high luster.

For determination of the compressive strength of the core and jacket of the dental prosthesis element according to the invention, samples of the core and jacket materials described in examples 1-6 are placed in glass tubes (inside diameter 4 mm, height 8 mm) and exposed for to light 360 seconds with the Dentacolor XS lamp. The polymeric test bodies thus obtained are removed from the glass test tubes and stored for 24 hours in water at 37° C. Then their compressive strength is measured in accordance with the Australian standard for dental filling materials, AS 1278-1973.

Furthermore, polymeric test bodies 25×2×2 mm are prepared from samples of the core and jacket materials described in examples 1-6. The flexural strength and bending modulus of the test bodies are ascertained in accordance with DIN 13 922.

The figures obtained for compressive strength, flexural strength and bending modulus are listed in the following table. "particle size" means "average particle size" (with regard to the invention)

TABLE

| (a) core material<br>(b) jacket material | compressive strength [MPa] | flexural strength [MPa] | bending modulus [MPa] |
| --- | --- | --- | --- |
| (a) | | | |
| Example 1 | 400 | 180 | 19000 |
| Example 2 | 380 | 160 | 18050 |
| Example 3 | 420 | 183 | 17800 |
| (b) | | | |
| Example 4 | 400 | 65 | 3500 |
| Example 5 | 420 | 80 | 3600 |
| Example 6 | 400 | 90 | 3900 |

What is claimed is:

1. A plastic dental prosthesis element for crowns, bridges and inlays comprising a core formed of a plastic material comprising an 70-10% by weight of an acrylate or methacrylate or mixture thereof based polymer containing 30-90% by weight of an inorganic filler, said inorganic filler being comprised of 60-100% of an inorganic dental filler material selected from the group consisting of silicon dioxide, lithium aluminum silicate glass, strontium aluminum silicate glass and a mixture thereof, and having a particle size of from 0.7-5 micrometers, and 0-40% by weight of microdispersed silicon dioxide having a particle size from 0.01 to 0.04 micrometers, and a jacket disposed over said core and being formed of a plastic material comprising 90-10% by weight of an acrylate, methacrylate or mixture thereof based polymer containing 10-90% by weight of microdispersed silicon dioxide having a particle size of 0.01 to 0.4 micrometers as the sole filler, said core having a mechanical strength greater than the mechanical strength of the jacket, whereby thin-walled shapes and slender embodiment of the prosthesis element are enabled, said core having a flexural strength of 160 to 183 MPa and having a bending modulus of 17,800 to 19,000 MPa and said jacket having a flexural strength of 65 to 90 MPa having a bending modulus of 3500 to 3900 MPa.

2. The dental prosthesis element of claim 1, wherein said core contains from 60-85% by weight of the inorganic filler, said inorganic filler comprising a mixture of from 80-90% by weight of said inorganic dental filler material and from 10-20% by weight of said microdispersed silicon dioxide; and said jacket contains from 30-70% by weight of said microdispersed silicon dioxide;

said microdispersed silicon dioxide having a mean particle size of from 0.01-0.04 micrometers and said inorganic filler material being silicon dioxide, lithium aluminum silicate glass, strontium aluminum silicate glass or a mixture thereof.

3. The dental prosthesis element of claim 2 wherein said inorganic filler material and said microdispersed silicon dioxide are silanized.

4. The dental prosthesis element of claim 2 wherein the plastic material of the core and the plastic material of the jacket is a polymer selected from the group consisting of bis-GMA, ethoxylated bisphenol A diacrylate, ethoxylated bisphenol A dimethacrylate, triethylene glycol dimethacrylate, dodecane dioldimethacrylate, diurethane dimethacrylate from 2-hydroxy-ethylmethacrylate and 2,2,4-trimetylhexamethylene diisocyanate, bis(acryloyloxymethyl)tricyclo[5.2.1.0$^{2,6}$]decane and bis(methacryloyloxymethyl)tricyclo[5.2.1.0$^{3,6}$]decane.

5. The dental prosthesis element of claim 2 wherein the plastic material of the core is a polymer of esters of acrylic acid or a mixture thereof methacrylic acid with bivalent or multivalent alcohols, or mixtures thereof, comprising from 20-85% by weight of bis-GMA or ethoxylated bisphenol A dimethacrylate; and the plastic material of the jacket contains a polymer of esters of acrylic acid or methacrylic acid or mixtures thereof with bivalent or multivalent alcohols, or mixtures thereof comprising, from 20-70% by weight of a diurethane dimethacrylate from 2-hydroxyethylmethacrylate and 2,2,4-trimethylhexamethylene diisocyanate.

6. The dental prosthesis element of claim 5 wherein the plastic material of the jacket further contains a polymer of dodecanediol dimethacrylate.

7. The dental prosthesis element of claim 2 wherein the plastic material of the core is a polymer of esters of acrylic acid or methacrylic acid or a mixture thereof, with bivalent or multivalent alcohols or a mixture thereof, comprising 20-85% by weight of bis-GMA or ethoxylated bisphenol A dimethacrylate, and
   the plastic material of the jacket contains a polymer of esters of acrylic acid or methacrylic acid or a mixture thereof, with bivalent or multivalent alcohols or a mixture thereof, comprising from 20-70% by weight of a diurethane dimethacrylate from 2-hydroxyethylmethacrylate and 2,2,4-trimethylhexamethylene diisocyanate and from 20-40% by weight of bis(methacryloyloxymethyl) tricyclo[5.2.1.0$^{2,6}$]-decane.

8. The dental prosthesis element claimed in claim 7 wherein the plastic material of the jacket additionally contains a polymer of dodecanediol dimethacrylate.

9. The dental prosthesis element of claim 1, wherein the core contains from 60-85% by weight of the inorganic filler.

10. The dental prosthesis of claim 9, wherein the inorganic filler comprises a mixture of from 80-90% by weight of the inorganic filler material and from 10-20% by weight of the microdispersed silicon dioxide.

11. The dental prosthesis element of claim 9, wherein the jacket contains from 30-70% by weight of microdispersed silicon dioxide.

12. The dental prosthesis element as claimed in claim 11, wherein the microdispersed silicon dioxide has a particle size of from 0.01-0.04 micrometers.

13. The dental prosthesis element of claim 9 wherein the plastic material of the core and of the jacket comprises polymeric esters of acrylic acid or methacrylic acid or a mixture thereof, with bivalent or multivalent alcohols of a mixture thereof.

14. The dental prosthesis of claim 13 wherein the plastic material is a polymer of bis-GMA, ethoxylated bisphenol A diacrylate, ethoxylated bisphenol A dimethacrylate, triethylene glycol dimethacrylate, dodecanediol dimethacrylate, diurethane dimethacrylate from 2-hydroxyethylmethacrylate and 2,2,4-trimethylhexamethylene diisocyanate, bis(acryloyloxymethyl) tricyclo[5.2.1.0$^{2,6}$]decane or bis(methacryloyloxymethyl)tricyclo[5.2.1.0$^{2,6}$) decane.

15. The dental prosthesis element of claim 14 wherein the plastic material of the core is a polymer of esters of acrylic acid or methacrylic acid or a mixture thereof with bivalent or multivalent alcohols or a mixture thereof, comprising from 20-85% by weight of bis-GMA or ethoxylated bisphenol A dimethacrylate.

16. The dental prosthesis element of claim 14 wherein the plastic material of the jacket contains a polymer of esters of acrylic acid or methacrylic acid or a mixture thereof, with bivalent or multivalent alcohols or a mixture thereof, comprising from 20-70% by weight of the diurethane dimethacrylate from 2-hydroxyethylmethacrylate and 2,2,4-trimethylhexamethylene diisocyanate.

17. The dental prosthesis element of claim 14 wherein the plastic material of the jacket contains a polymer of esters of acrylic acid or methacrylic acid or a mixture thereof, with bivalent or multivalent alcohols or a mixture thereof, comprising from 20-70% by weight of the diurethane dimethacrylate from 2-hydroxyethylmethacrylate and 2,2,4-trimethylhexamethylene diisocyanate and from 20-40% by weight of bis(methacryloyloxymethyl)tricyclo[5.2.1.0$^{2,6}$]-decane.

18. The dental prosthesis element as claimed in claim 17 wherein the plastic material of the jacket additionally contains a polymer of dodecanediol dimethacrylate.

19. The dental prosthesis element of claim 1, wherein the jacket and the core each further comprise 0.1 to 0.5% by weight of one or more photopolymerization catalysts selected from the group consisting of camphor quinone, a benzil acetal and an amine.

20. The dental prosthesis element of claim 19, wherein the core comprises
   4.5% by weight of bis-GMA,
   10.5% by weight of triethylene glycol dimethacrylate,
   72.6% by weight of lithium aluminum silicate glass having a particle size of 5 micrometers,
   12.0% by weight of microdispersed silicone dioxide, having a particle size of 0.04 micrometers,
   0.1% by weight of camphor quinone,
   0.1% by weight of benzil dimethylacetal and
   0.2% by weight of p-dimethylaminoethyl benazoate.

21. The dental prosthesis element of claim 19, wherein the core comprises
   12.4% by weight of ethoxylated bisphenol A diacrylate,
   2.8% by weight of trimethylolpropane triacrylate,
   71.2% by weight of lithium aluminum aluminum silicate glass having a particle size of 5 micrometers,
   13.2% by weight of microdispersed silicone dioxide, having a particle size of 0.04 micrometers, silanized with 3-methacryloyl-oxypropyltrimethoxysilane,
   0.1% by weight of camphor quinone,
   0.1% by weight of benzil dimethylacetal and 0.2% by weight of p-dimethylaminoethyl benazoate.

22. The dental prosthesis element of claim 19, wherein the core comprises 12.1% by weight of ethoxylated bisphenol A dimethacrylate,
3.0% by weight of hexamethylenedioldimethacrylate,
79.8% by weight of lithium aluminum silicate glass having a particle size of 5 micrometers,
4.7% by weight of microdispersed silicone dioxide, having a mean particle size of 0.04 micrometers, silanized with 3-methacrylyloxypropyltrimethoxysilane,
0.1% by weight of camphor quinone,
0.1% by weight of benzil dimethylacetal and
0.2% by weight of p-dimethylaminoethyl benzoate.

23. The dental prosthesis element of claim 19, wherein the jacket comprises
11.3% by weight of diurethane dimethacrylate obtained from 2 moles of 2-hydroxyethylmethacrylate and 1 mole of 2,2,4-trimethylhexamethylene diisocyanate,
7.6% of bis-GMA,
3.4% by weight of triethylene glycol dimethacrylate,
27.0% by weight of microdispersed silicone dioxide, having a particle size of 0.04 micrometers, silanized with 3-methacryloyloxypropyltrimethoxysilane,
50.0% by weight of splinter polymerizate, having a particle size of 40 micrometers,
0.1% by weight of camphor quinone,
0.1% by weight of benzil dimethylacetal,
0.2% by weight of p-dimethylaminoethyl benzoate and
0.3% by weight of pigments.

24. The dental prosthesis element of claim 19, wherein the jacket comprises
19.3% by weight of bis(acryloyloxymethyl)tricyclo-(5.2.1.0$^{2,6}$)decane,
28.1% by weight of microdispersed silicone dioxide, having a particle size of 0.04 micrometers, silanized with 3-methacryloyloxypropyltrimethoxysilane,
52.0% by weight of splinter polymerizate, having a particle size of 40 micrometers,
0.1% by weight of camphor quinone
0.1% by weight of benzil dimethylacetal,
0.2% by weight of p-dimethylaminoethyl benzoate and
0.2% by weight of pigments.

25. The dental prosthesis element of claim 19, wherein the jacket comprises
19.3% by weight of bis(methacryloyloxymethyl)-tricyclo-(5.2.1.0$^{2,6}$)decane,
28.1% by weight of microdispersed silicone dioxide, having a particle size of 0.04 micrometers, silanized with 3-methacryloyloxypropyltrimethoxysilane,
52.0% by weight of splinter polymerizate, having a particle size of 40 micrometers,
0.1% by weight of camphor quinone,
0.1% by weight of benzil dimethylacetal,
0.2% by weight of p-dimethylaminoethyl benzoate and
0.2% by weight of pigments.

* * * * *